United States Patent
Hsiao et al.

(10) Patent No.: US 8,500,791 B2
(45) Date of Patent: *Aug. 6, 2013

(54) STENT DESIGNS FOR USE IN PERIPHERAL VESSELS

(75) Inventors: Hao-Ming Hsiao, Cupertino, CA (US);
Keif Fitzgerald, San Jose, CA (US);
Boris Anukhin, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/557,303

(22) Filed: Jul. 25, 2012

(65) Prior Publication Data
US 2012/0296410 A1 Nov. 22, 2012

Related U.S. Application Data

(63) Continuation of application No. 11/844,235, filed on Aug. 23, 2007, now Pat. No. 8,252,041.

(60) Provisional application No. 60/823,352, filed on Aug. 23, 2006.

(51) Int. Cl.
*A61F 2/06* (2013.01)

(52) U.S. Cl.
USPC .......................................................... 623/1.11

(58) Field of Classification Search
USPC ................ 623/1.11, 1.15–1.2, 1.23; 606/191, 606/194, 198, 200
See application file for complete search history.

(56) References Cited

U.S. PATENT DOCUMENTS

| | | |
|---|---|---|
| 3,868,956 A | 3/1975 | Alfidi et al. |
| 4,512,338 A | 4/1985 | Balko et al. |
| 4,553,545 A | 11/1985 | Maass et al. |
| 4,580,568 A | 4/1986 | Gianturco et al. |
| 4,655,771 A | 4/1987 | Wallsten |
| 4,665,906 A | 5/1987 | Jervis |
| 4,733,665 A | 3/1988 | Palmaz |
| 4,739,762 A | 4/1988 | Palmaz |
| 4,762,128 A | 8/1988 | Rosenbluth |
| 4,800,882 A | 1/1989 | Gianturco |

(Continued)

FOREIGN PATENT DOCUMENTS

WO    WO 00/62708    10/2000

OTHER PUBLICATIONS

U.S. Appl. No. 11/844,235, Jul. 24, 2012 Issue Fee payment.
U.S. Appl. No. 11/844,235, Apr. 27, 2012 Notice of Allowance.

(Continued)

*Primary Examiner* — Ryan Severson
*Assistant Examiner* — Katherine M Shi
(74) *Attorney, Agent, or Firm* — Baker Botts LLP

(57) ABSTRACT

System including a delivery catheter and a stent disposed at a distal end of the delivery catheter. The stent includes a plurality of radially expandable rings disposed adjacent to one another to define a tubular member having a proximal end portion, and a distal end portion, and a middle portion, each of the radially expandable rings including a plurality of strut members. The middle portion of the tubular member include a plurality of interconnection members extending between longitudinally adjacent expandable rings, the number of the plurality of the interconnection members being greater than that of the end portion of the tubular member. The stent also includes a transition section between the end portion and the middle portion, the transition section including at least one open cell and at least one closed cell. The stent can be self-expandable or balloon expandable.

20 Claims, 10 Drawing Sheets

U.S. PATENT DOCUMENTS

| | | | |
|---|---|---|---|
| 4,830,003 | A | 5/1989 | Wolff et al. |
| 5,067,957 | A | 11/1991 | Jervis |
| 5,158,548 | A | 10/1992 | Lau et al. |
| 5,421,955 | A | 6/1995 | Lau et al. |
| 5,514,154 | A | 5/1996 | Lau et al. |
| 5,569,295 | A | 10/1996 | Lam |
| 5,591,197 | A | 1/1997 | Orth et al. |
| 5,759,192 | A | 6/1998 | Saunders |
| 5,780,807 | A | 7/1998 | Saunders |
| 5,827,321 | A | 10/1998 | Roubin |
| 5,911,754 | A | 6/1999 | Kanesaka et al. |
| 6,375,676 | B1 | 4/2002 | Cox |
| 6,537,311 | B1 | 3/2003 | Cox et al. |
| 6,569,194 | B1 | 5/2003 | Pelton |
| 6,814,749 | B2 | 11/2004 | Cox et al. |
| 6,875,227 | B2 | 4/2005 | Yoon |
| 7,803,179 | B2 | 9/2010 | Denison |
| 8,252,041 | B2 | 8/2012 | Hsiao et al. |
| 2004/0243216 | A1 | 12/2004 | Gregorich |
| 2007/0191926 | A1 | 8/2007 | Nikanorov et al. |

OTHER PUBLICATIONS

U.S. Appl. No. 11/844,235, Jan. 30, 2012 Response to Non-Final Office Action.
U.S. Appl. No. 11/844,235, Sep. 30, 2011 Non-Final Office Action.
U.S. Appl. No. 11/844,235, Aug. 2, 2010 Amendment and Request for Continued Examination (RCE).
U.S. Appl. No. 11/844,235, Mar. 31, 2010 Final Office Action.
U.S. Appl. No. 11/844,235, Nov. 2, 2009 Response to Non-Final Office Action.
U.S. Appl. No. 11/844,235, Jun. 1, 2009 Non-Final Office Action.
U.S. Appl. No. 11/844,235, May 12, 2009 Amendment and Request for Continued Examination (RCE).
U.S. Appl. No. 11/844,235, Jan. 12, 2009 Final Office Action.
U.S. Appl. No. 11/844,235, Oct. 29, 2008 Response to Non-Final Office Action.
U.S. Appl. No. 11/844,235, Jul. 29, 2008 Non-Final Office Action.

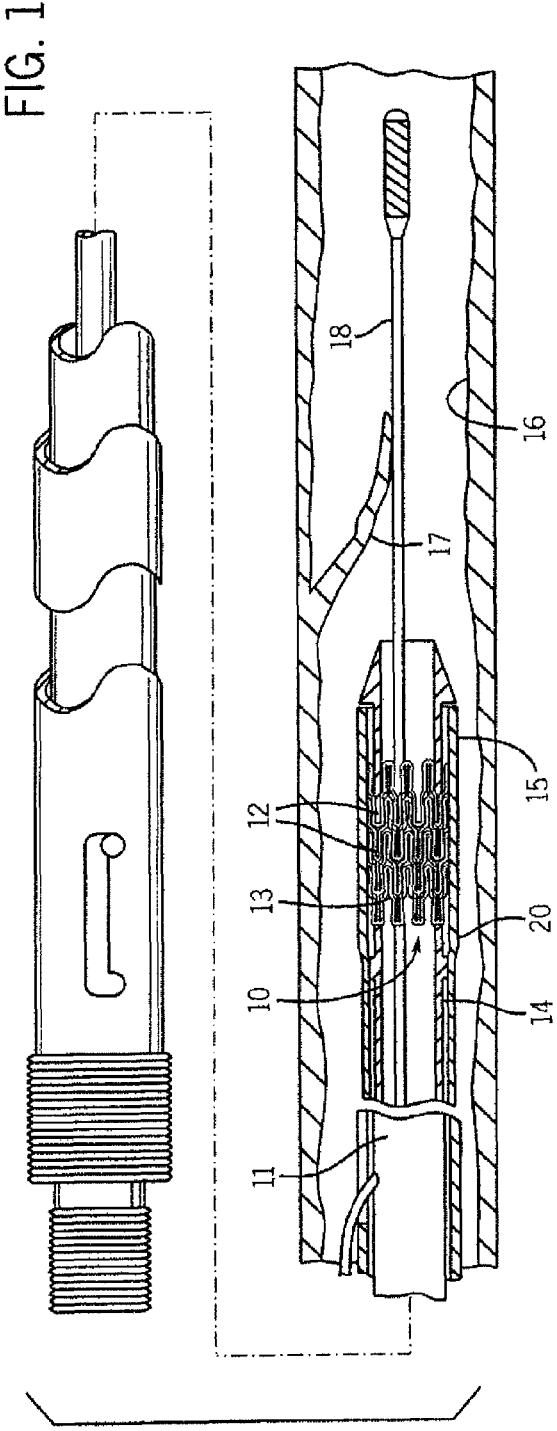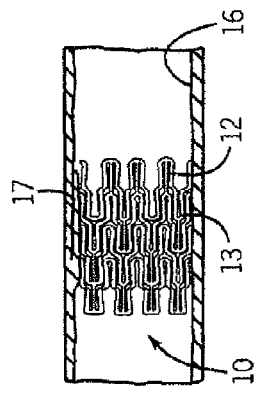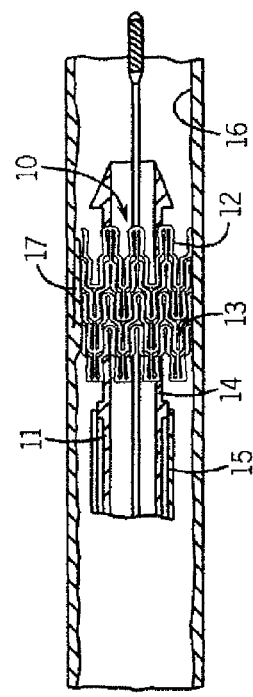

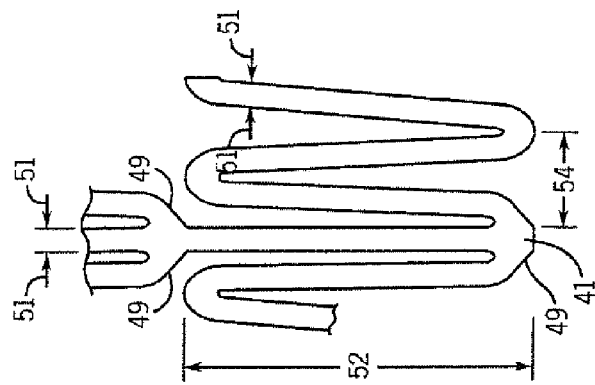
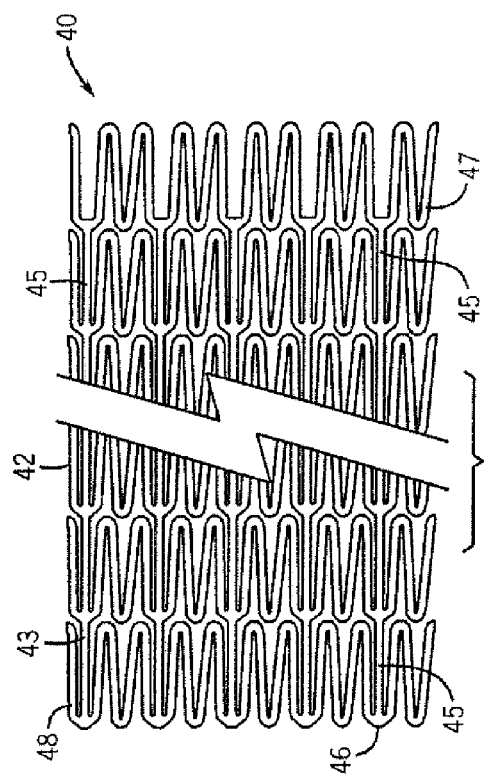
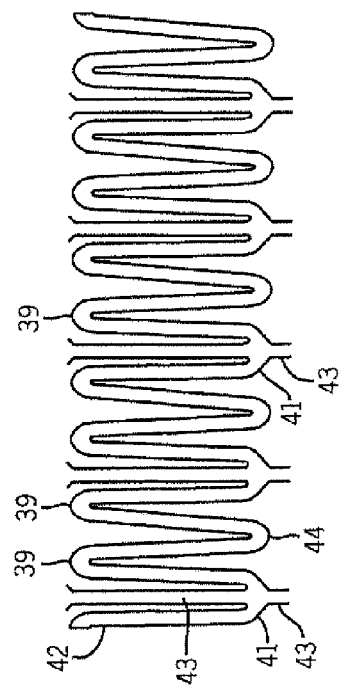

STENT DESIGNS FOR USE IN PERIPHERAL VESSELS

CROSS REFERENCE TO RELATED APPLICATIONS

This application is a continuation of U.S. application Ser. No. 11/844,235, filed Aug. 23, 2007, now U.S. Pat. No. 8,252,041 which claims the benefit of U.S. provisional application Ser. No. 60/823,352 filed Aug. 23, 2006, the disclose of each of which is incorporated by reference in its entirety herein.

FIELD OF THE INVENTION

The present invention relates to expandable endoprosthesis devices, generally called stents, which are adapted to be implanted into a patient's body lumen, such as a blood vessel, to maintain the patency thereof. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis.

BACKGROUND OF THE INVENTION

Stents, grafts and a variety of other endoprosthesis are well known and used in interventional procedures, such as for treating aneurysms, for lining or repairing vessel walls, for Stents are generally cylindrically-shaped devices which function to hold open and sometimes expand a segment of a blood vessel or other arterial lumen, such as coronary artery. Stents are usually delivered in a compressed condition to the target site and then deployed at that location into an expanded condition to support the vessel and help maintain it in an open position. They are particularly suitable for use to support and hold back a dissected arterial lining which can occlude the fluid passageway there through.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted into a compressed state for deployment into a body lumen. One of the difficulties encountered in using prior art stents involve maintaining the radial rigidity needed to hold open a body lumen while at the same time maintaining the longitudinal flexibility of the stent to facilitate its delivery and accommodate the often tortuous path of the body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from shape memory metals or super-elastic nickel-titanium (NiTi) alloys, which will automatically expand from a compressed state when the stent is advanced out of the distal end of the delivery catheter into the blood vessel. Such stents manufactured from expandable heat sensitive materials allow for phase transformations of the material to occur, resulting in the expansion and contraction of the stent.

Details of prior art expandable stents can be found in U.S. Pat. No. 3,868,956 (Alfidi et al.); U.S. Pat. No. 4,512,1338 (Balko et al.); U.S. Pat. No. 4,553,545 (Maas, et al.); U.S. Pat. No. 4,733,665 (Palmaz); U.S. Pat. No. 4,762,128 (Rosenbluth); U.S. Pat. No. 4,800,882 (Gianturco); U.S. Pat. No. 5,514,154 (Lau, et al.); U.S. Pat. No. 5,421,955 (Lau et al.); U.S. Pat. No. 5,603,721 (Lau et al.); U.S. Pat. No. 4,655,772 (Wallstent); U.S. Pat. No. 4,739,762 (Palmaz); and U.S. Pat. No. 5,569,295 (Lam), which are hereby incorporated by reference in their entirety.

Further details of prior art self-expanding stents can be found in U.S. Pat. No. 4,580,568 (Gianturco); U.S. Pat. No. 4,830,003 (Wolff, et al.); U.S. patent application Ser. No. 10/158,362 (Denison); and U.S. Pat. Nos. 6,537,311 and 6,814,749 (Cox, et al.), which are hereby incorporated by reference in their entirety.

Expandable stents are delivered to the target site by delivery systems which often use balloon catheters as the means for delivering and expanding the stent in the target area. One such stent delivery system is disclosed in U.S. Pat. No. 5,158,548 to Lau et al., which is hereby incorporated by reference in its entirety. Such a stent delivery system has an expandable stent in a contracted condition placed on an expandable member, such as an inflatable balloon, disposed on the distal portion of an elongated catheter body. A guide wire extends through an inner lumen within the elongated catheter body and out its distal end. A tubular protective sheath is secured by its distal end to the portion of the guide wire which extends out of the distal end of the catheter body and fits over the stent mounted on the expandable member on the distal end of the catheter body.

Some prior art stent delivery systems for implanting self-expanding stents include an inner lumen upon which the compressed or collapsed stent is mounted and an outer restraining sheath which is initially placed over the compressed stent prior to deployment. When the stent is to be deployed in the body vessel, the outer sheath is moved in relation to the inner lumen to "uncover" the compressed stent, allowing the stent to move to its expanded condition into the target area.

In many procedures which utilize stents to maintain the patency of the patient's body lumen, the size of the body lumen can be quite small which prevents the use of some commercial stents which have profiles which are entirely too large to reach the small vessel. In particular, often in PTCA procedures, the stenosis is located in the very distal regions of the coronary arteries which often have small diameters. Many of these distal lesions are located deep within the tortuous vasculature of the patient which requires the stent to not only have a small profile, but also high flexibility to be advanced into these regions. As a result, the stent must be sufficiently flexible along its longitudinal axis, yet be configured to expand radially to provide sufficient strength and stability to maintain the patency of the body lumen. Since many commercial stents lack both the low profile and extreme flexibility needed to reach such distal lesions, they are not available for utilization for such procedures.

What has been needed is a stent which has a low profile and a high degree of flexibility so that it can be advanced through tortuous passage ways of the anatomy and can be expanded within the body vessel to maintain the patency of the vessel. Additionally, the expanded stent must have adequate structural strength (hoop strength) to hold the body lumen open once expanded. Such a stent should also have sufficient radiopaque properties to permit it to be sufficiently visualized on external monitoring equipment, such as a fluoroscope, to allow the physician to place the stent in the exact target location. The present invention satisfies these and other needs.

SUMMARY OF THE INVENTION

The present invention is directed to stents having low profiles which can be used in body vessels, such as the carotid arteries and other peripheral arteries, along with the coronary arteries. The stents of the present invention are intended, but are not limited, to the effective treatment of diseased vessels having diameters from about 3.0 to 14.0 millimeters.

The stents of the present invention can be formed from super elastic nickel titanium alloys, or other shape memory materials, which allow the stent to be self expandable. The expansion occurs when the stress of compression is removed. This allows the phase transformation from martensite to austenite to occur, and as a result the stent expands. The stents of the present invention can be processed to behave superelastically at body temperature. Alternatively, the stent designs of the present invention could be used in conjunction with balloon expandable stents made from stainless steel or other conventional stent materials.

In all embodiments, the stents of the present invention have sufficient longitudinal flexibility along their longitudinal axis to facilitate delivery through tortuous body lumens, yet remain stable when expanded radially to maintain the patency of a body lumen, such as an artery or other vessel, when implanted therein. The present invention particularly relates to unique strut patterns which have a high degree of longitudinal flexibility and conformability, while providing sufficient radial-expansibility and strength to hold open the body lumens. The high radial strength possessed by the stents of the present invention allow them to be used in treating calcified lesions.

Generally, the greater the longitudinal flexibility of the stents, the easier and the more safely they can be delivered to the implantation site, particularly where the implantation site is on a curved section of a body lumen, such as a coronary artery or peripheral blood vessel, and especially in saphenous veins and larger vessels. The designs of the present invention have sufficient flexibility to conform to the patient's vasculature, thus preventing vessel straightening by the stent. Moreover, the stents of the present invention are crush proof, making them particularly suitable for implantation in the carotid arteries.

Each of the different embodiments of stents of the present invention include a plurality of adjacent cylindrical elements (often referred to as "rings") which are generally expandable in the radial direction and arranged in alignment along a longitudinal stent axis. The cylindrical elements are formed in a variety of serpentine wave patterns transverse to the longitudinal axis and contain a plurality of alternating peaks and valleys. At least one interconnecting member (often referred to as a "spine") extends between adjacent cylindrical elements and connects them to one another. These interconnecting members insure minimal longitudinal contraction during radial expansion of the stent in the body vessel. The serpentine patterns have varying degrees of curvature in the regions of peaks and valleys and are adapted so that radial expansion of the cylindrical elements are generally uniform around their circumferences during expansion of the stent from the collapsed position to the expanded position.

The stents of the present invention also have strut patterns which enhance the strength of the ends of the stent and the overall radiopacity of the stent, yet retain high longitudinal flexibility along their longitudinal axis to facilitate delivery through tortuous body lumens and remain stable when expanded radially to maintain the patency of the body lumen. The present invention in particular relates to stents with unique end portions having sufficient hoop strength to maintain a constant inner diameter which prevents the stent from taking on a "cigar" shape when deployed in the body lumen. The end rings used with the present invention are particularly useful on self-expanding stents which may otherwise have end rings that are more susceptible to compressive forces.

The resulting stent structures are a series of radially expandable cylindrical elements that are spaced longitudinally close enough so that small dissections in the wall of a body lumen may be pressed back into position against the luminal wall, but not so close as to compromise the longitudinal flexibility of the stent both when negotiating through the body lumens in their unexpanded state and when expanded into position within the vessel. The design of the stents contribute to form small gaps between struts to minimize tissue prolapse. Each of the individual cylindrical elements may rotate slightly relative to their adjacent cylindrical elements without significant deformation, cumulatively providing stents which are flexible along their length and about their longitudinal axis, but which still are very stable in their radial direction in order to resist collapse after expansion.

In one embodiment of the present invention, each cylindrical element of the stent includes eight peak regions (often referred to as "crowns") and eight valley regions which provide sufficient coverage of the vessel when placed in the expanded or deployed position. In this design, each cylindrical element consisting of an alternating pattern of U-shaped portions and double-curved (W) portions connected both axially and circumferentially to eight discontinuous interconnecting members or spines. For example, the U-shaped portion of the cylindrical element can be connected to an adjacent cylindrical element via the interconnecting members. The same cylindrical element can be then connected to another cylindrical element via the interconnecting members connected to the double-curved portions. The cylindrical element can be connected to an adjacent cylindrical element by four interconnecting members. This particular alignment of interconnecting members provides adequate flexibility to the stent and also helps prevent foreshortening of the stent as it expands radially outward. The discontinuing pattern of interconnecting members results in a highly flexible stent that does not kink upon bending. Both the distal and proximal ends of this stent design can be entirely composed of "W" patterns which provide additional strength to the ends of the stent. The resulting stent produces an eight crown, four-cell pattern which has sufficient coverage for vessel scaffolding while maintaining excellent flexibility to reach distal lesions and possessing sufficient radial strength to hold the target vessel open. An alternative pattern using six crowns and six discontinuous interconnecting members also can be utilized and will exhibit these same physical properties.

The serpentine pattern of the individual cylindrical elements can optionally be in phase with each other in order to reduce the contraction of the stent along their length when expanded. In these embodiments of the present invention, interconnecting members align behind each other to create a continuous "spine" which extends from one end of the stent to the other. Two or three rows of continuous spines can be used to connect adjacent cylindrical elements. This construction also helps prevent the stent from foreshortening when expanded.

A stent made in accordance with the present invention can be readily delivered to the desired target location by mounting it on a stent delivery catheter which includes a retractable sheath, or other means, to hold the stent in its collapsed position prior to deployment.

These and other features and advantages of the present invention will become more apparent from the following detailed description of the invention, when taken in conjunction with the accompanying exemplary drawings.

DETAILED DESCRIPTION OF THE DRAWINGS

FIG. 1 is an elevational view, partially in section, depicting the stent embodying features of the present invention mounted on a delivery catheter disposed within a vessel.

FIG. 2 is an elevational view, partially in section, similar to that shown in FIG. 1, wherein the stent is expanded within a vessel, pressing the lining against the vessel wall.

FIG. 3 is an elevational view, partially in section, showing the expanded stent within the vessel after withdrawal of the delivery catheter.

FIG. 10 is a plan view of an alternative embodiment of a flattened stent of the present invention, which illustrates the serpentine pattern along with the peaks and valleys which form the cylindrical elements of the stent and permit the stent to achieve a small crimp profile, yet is expandable to a larger diameter to maintain the patency of a small vessel.

FIG. 11 is an enlarged partial view of the stent of FIG. 10 depicting the serpentine pattern along with the peaks and valleys which form another preferred embodiment of a cylindrical element made in accordance with the present invention.

FIG. 12 is an enlarged view of a double-curved portion (w) which has a sweep cut which helps the stent to be crimped to a low diameter.

DETAILED DESCRIPTION OF PREFERRED EMBODIMENTS

Prior art stent designs, such as the MultiLink Stent™ manufactured by Advanced Cardiovascular Systems, Inc., Santa Clara, Calif., include a plurality of cylindrical rings that are connected by three connecting members between adjacent cylindrical rings. Each of the cylindrical rings is formed of a repeating pattern of U-, Y-, and W-shaped members, typically having three repeating patterns forming each cylindrical element or ring. A more detailed discussion of the configuration of the MultiLink Stent™ can be found in U.S. Pat. No. 5,569,295 (Lam) and U.S. Pat. No. 5,514,154 (Lau et al.), whose contents are hereby incorporated by reference.

Figure 4:
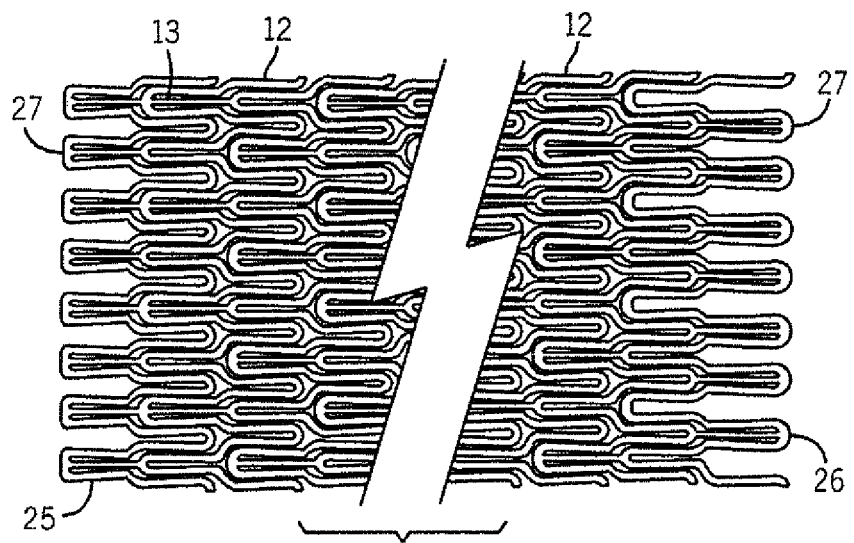
FIG. 4 is a plan view of one preferred embodiment of a flattened stent of the present invention, which illustrates the serpentine pattern including peaks and valleys which form the cylindrical elements of the stent and permit the stent to achieve a small crimp profile, yet is expandable to a larger diameter to maintain the patency of a small vessel.

Beyond those prior art stents, FIG. 1 illustrates an exemplary embodiment of stent 10 incorporating features of the present invention, which stent is mounted onto delivery catheter 11. FIG. 4 is a plan view of this exemplary embodiment stent 10 with the structure flattened out into two dimensions to facilitate explanation. Stent 10 generally comprises a plurality of radially expandable cylindrical elements 12 disposed generally coaxially and interconnected by interconnecting members 13 disposed between adjacent cylindrical elements 12. The delivery catheter 11 has an inner tubular member 14 upon which the collapsed stent 10 is mounted. A restraining sheath 15 extends over both the inner tubular member 14 and stent 10 in a co-axial relationship. The stent delivery catheter 11 is used to position the stent 10 within an artery 16 or other vessel. The artery 16, as shown in FIG. 1, has a dissected or detached lining 17 which has occluded a portion of the arterial passageway.

In a preferred embodiment, the delivery of the stent 10 is accomplished in the following manner. Stent 10 is first mounted onto the delivery catheter 11 with the restraining sheath placed over the collapsed stent. The catheter-stent assembly can be introduced within the patient's vasculature in a conventional Seldinger technique through a guiding catheter (not shown). A guide wire 18 is disposed through the damaged arterial section with the detached or dissected lining 17. The catheter-stent assembly is then advanced over guide wire 18 within artery 16 until the stent 10 is directly under the detached lining 17. The restraining sheath 15 is retracted exposing the stent 10 and allowing it to expand against the inside of artery 16, which is illustrated in FIG. 2. While not shown in the drawing, artery 16 is preferably expanded slightly by the expansion of stent 10 to seat or otherwise embed stent 10 to prevent movement. Indeed, in some circumstances during the treatment of stenotic portions of an artery, the artery may have to be expanded considerably in order to facilitate passage of blood or other fluid there through.

While FIGS. 1-3 depict a vessel having detached lining 17, stent 10 can be used for purposes other than repairing the lining. Those other purposes include, for example, supporting the vessel, reducing the likelihood of restenosis, or assisting in the attachment of a vascular graft (not shown) when repairing an aortic abdominal aneurysm.

In general, stent 10 serves to hold open the artery 16 after catheter 11 is withdrawn, as illustrated in FIG. 3. Due to the formation of stent 10, the undulating component of the cylindrical elements of stent 10 is relatively flat in a transverse cross-section so that when stent 10 is expanded, cylindrical elements 12 are pressed into the wall of artery 16 and as a result do not interfere with the blood flow through artery 16.

Cylindrical elements 12 of stent 10 that are pressed into the wall of artery 16 will eventually be covered with endothelial cell growth that further minimizes blood flow turbulence. The serpentine pattern of cylindrical sections 12 provide good tacking characteristics to prevent stent movement within the artery. Furthermore, the closely spaced cylindrical elements 12 at regular intervals provide uniform support for the wall of artery 16, and consequently are well adapted to tack up and hold in place small flaps or dissections in the wall of artery 16 as illustrated in FIGS. 2 and 3.

Figure 5:
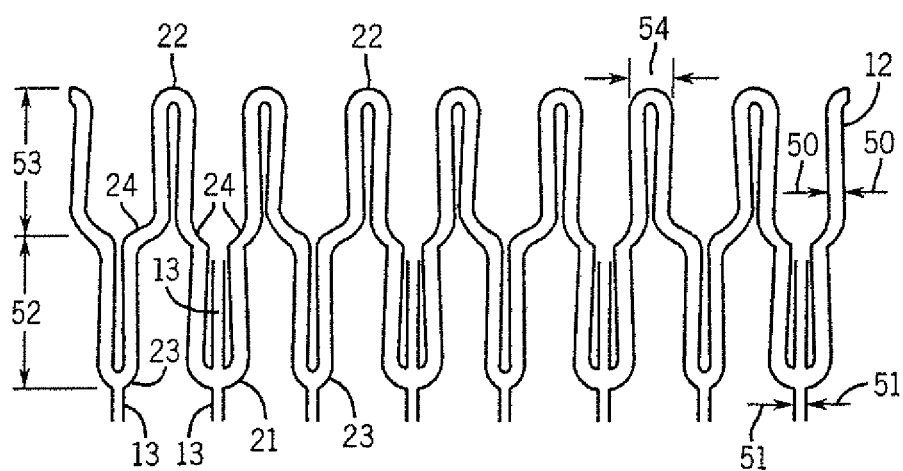
FIG. 5 is an enlarged partial view of the stent of FIG. 4 depicting the serpentine pattern along with the peaks and valleys which form one preferred embodiment of a cylindrical element made in accordance with the present invention.

The stresses involved during expansion from a low profile to an expanded profile are generally evenly distributed among the various peaks and valleys of stent 10. Referring now to FIGS. 4-5, one preferred embodiment of the present invention as depicted in FIGS. 1-3 is shown wherein each expanded cylindrical element 12 embodies a serpentine pattern having a plurality of peaks and valleys that aid in the even distribution of expansion forces. In this exemplary embodiment, interconnecting members 13 serve to connect adjacent valleys of each adjacent cylindrical element 12 as described above. The various peaks and valleys generally have U, W and inverted-U shapes, in a repeating pattern to form each cylindrical element 12. It should be appreciated that the cylindrical element 12 can be formed in different shapes without departing from the spirit and scope of the present invention.

The cylindrical element 12 of this stent 10 includes double-curved portions (W) 21 located in the region of the valley where each interconnecting member 13 is connected to an adjacent cylindrical element 12. The peak portions (inverted-U) 22 and the valley portions (U) 23 also form the cylindrical element 12 of the stent 10. A shoulder region 24 extending from each valley portion to peak portion (inverted U) 22 allows the peak portion to be nested in a tight formation next to an adjacent cylindrical element 12. This shoulder region 24 provides a transition region between the peak portions (inverted U) 22 and the valley portions (U) 23 and double-curved portion (W) 21 to allow adjacent cylindrical elements to nest within one another and thereby better support the artery walls with smaller gaps between stent struts. In this manner, the shoulder region 24 provides more dense coverage of the serpentine pattern of the cylindrical element to create a fairly uniform strut pattern which fully supports the walls of the diseased artery. For this reason, there are no or few areas of the stent wall which do not have struts for supporting the wall of the artery. Each of the valley portions (U) 23 forms a Y-shaped member when connected to an interconnecting member 13. As can be seen in this particular design, each of the valley portions (W's and U's) 21 and 23 have an interconnecting member which connects that cylindrical element 12 to an adjacent cylindrical element. As a result, each cylindrical element 12 is connected to an adjacent cylindrical element by at least four interconnecting members 13. The peak portions (inverted "U") 22 are not directly connected to any adjacent cylindrical element to allow for radial expansion. The eight interconnecting members 13 which are connected to each cylindrical element 12 are discontinuous with each other to produce a highly flexible stent that does not kink upon bending. This particular design allows the stent 10 to be placed in tortuous anatomy, where the stent 10 will conform to the particular anatomy of the patient. For example, if the stent 10 is placed in a curved portion of a artery, then the flexibility of the stent will allow it to take on the same curved shape without kinking and will still be capable of fully supporting the artery. Additionally, the stent's resistance to kinking helps prevent occlusion of the vessel lumen by the stent struts. Even though the stent 10 is flexible, it is still rigid when collapsed so that it can be placed on the delivery catheter and moved into the desired location in the patient's vasculature.

The stent 10 also includes end rings 25 and 26 which comprise all "W" shaped portions 27 to provide additional strength to the ends of the stent 10. This "W" pattern also helps to increase the overall radiopacity of the stent by virtue of the additional material needed to create such a "W" pattern. As a result, the stent 10 should be easily observable by a physician using imaging instrumentation, such as a fluoroscope.

Figure 6:
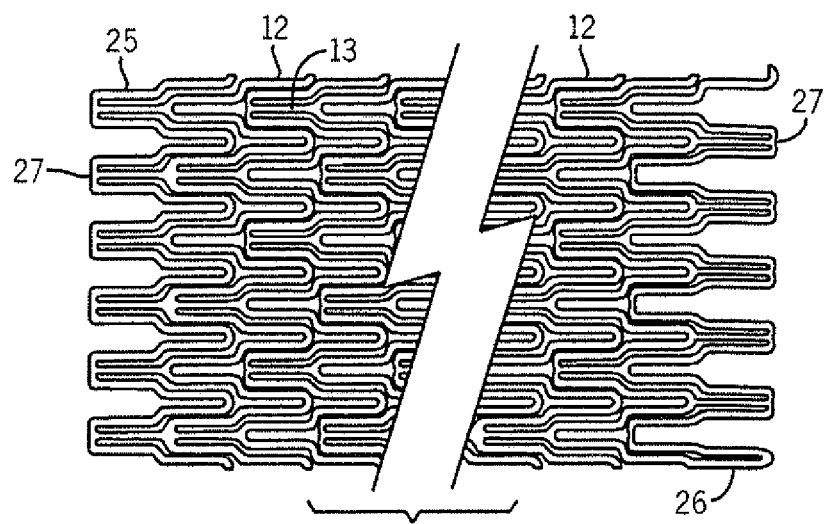
FIG. 6 is a plan view of an alternative embodiment of a flattened stent of the present invention, which illustrates the serpentine pattern along with the peaks and valleys which form the cylindrical elements of the stent and permit the stent to achieve a small crimp profile, yet is expandable to a larger diameter to maintain the patency of a small vessel.
Figure 7:
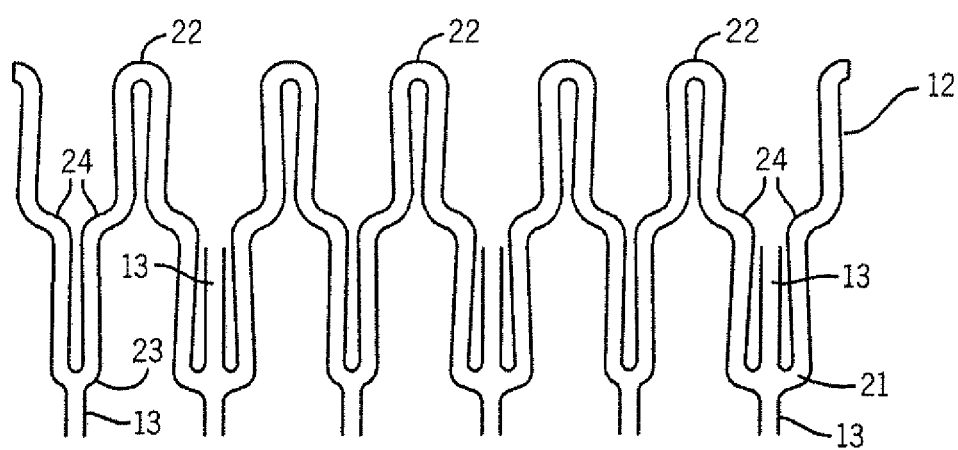
FIG. 7 is an enlarged partial view of the stent of FIG. 6 depicting the serpentine pattern along with the peaks and valleys which form another preferred embodiment of a cylindrical element made in accordance with the present invention.

In another embodiment of the present invention, as is shown in FIGS. 6 and 7, the stent 10 made with six crowns or peak portions (inverted U) 22, rather than the eight crowns shown in the previous embodiment. Otherwise, the strut pattern is virtually identical. The stent shown in FIGS. 6 and 7 include six valley portions, namely three valley portions (W) 21 and three valley portions (U) 23. This particular design also has six discontinuous interconnecting members 13 which connect each cylindrical element 12 to an adjacent cylindrical element. Again, the interconnecting member 13 are connected to each of the valley portions (W) 21 and valley portion (U) 23 to help prevent shortening of the stent during radio expansion. This pattern also helps increase the flexibility of the strut. End rings 25 and 26 which comprise of all "W" shaped portions 27 provide additional strength to the ends of the stent 10, while increasing the radiopacity of the stent as well.

Figure 8:
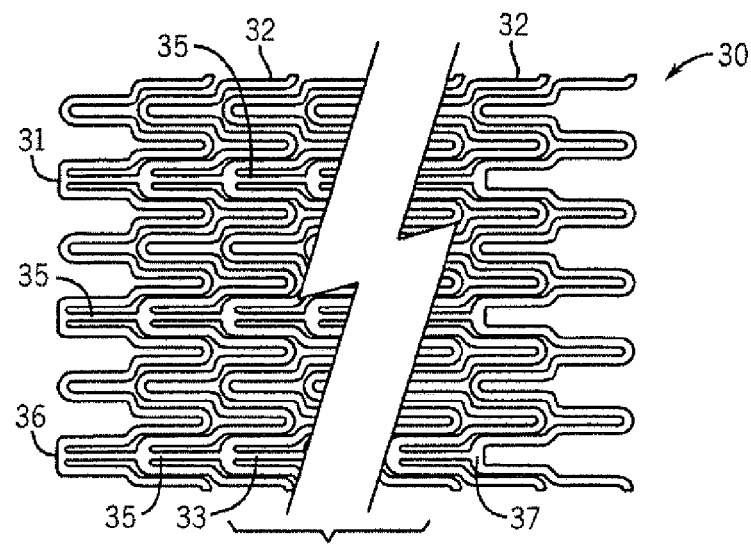
FIG. 8 is a plan view of an alternative embodiment of a flattened stent of the present invention, which illustrates the serpentine pattern along with the peaks and valleys which form the cylindrical elements of the stent and permit the stent to achieve a small crimp profile, yet is expandable to a larger diameter to maintain the patency of a small vessel.
Figure 9:
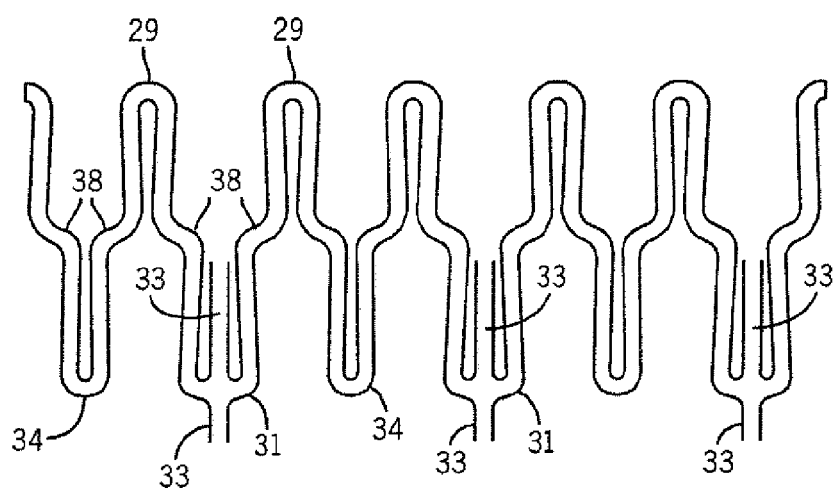
FIG. 9 is an enlarged partial view of the stent of FIG. 8 depicting the serpentine pattern along with the peaks and valleys which form another preferred embodiment of a cylindrical element made in accordance with the present invention.

In another embodiment of the invention, as shown in FIGS. 8 and 9, the stent 30 is made with cylindrical elements 32 which include six crowns or peak portions (inverted U's) 29 and six valley portions, namely three valley portions (W) 31 and three valley portions (U) 34. This particular design differs from the previous two embodiments by utilizing three continuous interconnecting members 33 which are utilized to connect each of the cylindrical elements 32 to an adjacent cylindrical element. Each interconnecting member 33 is connected to the valley portion (W) 31 which creates a continuous spine 35 which extends from one end 36 to the other end 37 of the stent 30. In this manner, the serpentine pattern of each individual cylindrical element 30 are in phase with each other in order to help reduce the contraction of the stent along their lengths when expanded. These continuous spines 35 help prevent the stent 30 from shortening when each of the cylindrical elements 30 are radially expanded.

The cylindrical element 32 also differs from the previous embodiments since a valley portion (U) 34 is not utilized to interconnect adjacent cylindrical elements to each other. However, the cylindrical element 32 includes a shoulder region 38 which extends between each of the valley portions and peak portions to provide a transition region which allows the peak portion (inverted U) 29 to be crimped in close proximity to an adjacent cylindrical element. In this manner, the stent 30 can be crimped down to a low profile which helps reduce the overall profile of the stent and delivery catheter when placing the stent 30 through the tortuous anatomy of the patient's vasculature.

In still another embodiment of the present invention, as is shown in FIGS. 10 and 11, a stent 40 is shown having a plurality of cylindrical elements 42 which are connected together by interconnecting members 43. Each of the cylindrical elements 42 include a peak portion (inverted U) 39 and valley portions (W) 41 and valley portions (U) 44 which form the composite ring. In this particular design, five valley portions (W) 41 are utilized and each of the cylindrical element 42 is connected to an adjacent cylindrical element 42 by an interconnecting member 43 which is connected to the valley portion (W) 41. As with the previous embodiment, each interconnecting member 43 extends directly behind one another to form a continuous spine 45 which extends from one end 46 to the other end 47 of the stent 40. In this particular embodiment, five continuous spines 45 are created on the composite stent 40. The peak portions (inverted U) 39 and the valley portion (U) 44 are not connected by any interconnecting members. The end ring 48 of this particular stent 40 includes five double curved portions (W) 41 which helps increase the radial strength of this end while enhancing the radiopacity as well. As can be seen from the single cylindrical element 42 shown in FIG. 11, the double curved portion (W) 41 include a "sweep cut" 49 which helps to reduce the collapsed profile of the stent 40 when it is placed on a delivery catheter. This reduced portion of the double curved portion (W) 21 enables the peak portion (inverted U) 39 to be collapsed closer to the double curved portion (W) 41 without hitting the double-curved portion (W) 41 when the stent 40 is crimped onto the delivery catheter. As a result, there should be no metal to metal contact when the stent is crimped and the stent 40 should be crimped on to an even smaller profile which again helps in reducing the over profile of the stent and delivery catheter and in reaching tight distal vessels. While this sweep cut 49 is shown only in conjunction with the embodiment shown in FIGS. 10 and 11, this sweep cut could be created on any of the other embodiments disclosed herein to help and reduce the overall diameter of the stents when they are being crimped on to the stent delivery catheters.

It should be appreciated that the present design can be made with a number of peaks and valleys ranging from 4 to 16. The number of peaks and valleys will depend upon the particular physical characteristics desired, along with the particular application to which the stent will be used.

In many of the drawing figures, the present invention stent is depicted flat, in a plan view for ease of illustration. All of the embodiments depicted herein are cylindrically-shaped stents that are generally formed from tubing by laser cutting as described below.

One important feature of all of the embodiments of the present invention is the capability of the stents to expand from a low-profile diameter to a larger diameter, while still maintaining structural integrity in the expanded state and remaining highly flexible. Stents of the present invention each have an overall expansion ratio of about 1.0 up to about 5.0 times the original diameter, or more, using certain compositions of materials. The stents still retain structural integrity in the expanded state and will serve to hold open the vessel in which they are implanted. Some materials may afford higher or lower expansion ratios without sacrificing structural integrity.

While the stent design of the present invention has very practical applications for procedures involving vessel diameters from about 3.0 to 14.0 millimeters, it should be appreciated that the stent pattern could also be successfully used in procedures involving larger lumens of the body, without departure from the spirit and scope of the present invention. Due to the increase of the longitudinal flexibility provided by the present stent design, such applications could include larger diameter vessels where added flexibility in reaching the vessel is needed.

The stents of the present invention can be made in many ways. However, the preferred method of making the stent is to cut a thin-walled tubular member, such as Nitinol tubing to remove portions of the tubing in the desired pattern for the stent, leaving relatively untouched the portions of the metallic tubing which are to form the stent. It is preferred to cut the tubing in the desired pattern by means of a machine-controlled laser.

A suitable composition of Nitinol used in the manufacture of a self expanding stent of the present invention is approximately 55% nickel and 44.5% titanium (by weight) with trace amounts of other elements making up about 0.5% of the composition. The austenite transformation temperature is between about −15.degree. C. and 30.degree. C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of Nitinol can be utilized, as can other self-expanding alloys, to obtain the same features of a self-expanding stent made in accordance with the present invention.

The stent of the present invention can be laser cut from a tube of super-elastic (sometimes called pseudo-elastic) nickel titanium (Nitinol) whose transformation temperature is below body temperature. All of the stent diameters can be cut with the same stent pattern, and the stent is expanded and heat treated to be stable at the desired final diameter. The heat treatment also controls the transformation temperature of the Nitinol such that the stent is super elastic at body temperature. The transformation temperature is at or below body temperature so that the stent will be superelastic at body temperature. The stent can be electro polished to obtain a smooth finish with a thin layer of titanium oxide placed on the surface. The stent is usually implanted into the target vessel which is smaller than the stent diameter so that the stent applies a force to the vessel wall to keep it open.

The stent tubing of a self expanding stent made in accordance with the present invention may be made of suitable biocompatible material besides super-elastic nickel-titanium (NiTi) alloys. In this case the stent would be formed full size but deformed (e.g. compressed) to a smaller diameter onto the balloon of the delivery catheter to facilitate intra luminal delivery to a desired intra luminal site. The stress induced by the deformation transforms the stent from an austenite phase to a martensite phase, and upon release of the force when the stent reaches the desired intra luminal location, allows the stent to expand due to the transformation back to the more stable austenite phase. Further details of how NiTi super-elastic alloys operate can be found in U.S. Pat. No. 4,665,906 (Jervis) and U.S. Pat. No. 5,067,957 (Jervis).

The tubing also may be made of suitable biocompatible material such as stainless steel. The stainless steel tube may be alloy-type: 316L SS, Special Chemistry per ASTM F138-92 or ASTM F139-92 grade 2.

The stent diameters are very small, so the tubing from which it is made must necessarily also have a small diameter. For PTCA applications, typically the stent has an outer diameter on the order of about 1 mm (0.04-0.09 inches) in the unexpanded condition, the same outer diameter of the hypotubing from which it is made, and can be expanded to an outer diameter of 4.0 mm or more. The wall thickness of the tubing is about 0.076-0.381 mm (0.003-0.015 inches). For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

Referring now to FIG. 5, the width of the strut of the cylindrical element, indicated by arrows 50, can be about from 0.003 to 0.009 inches. The width of the strut of the interconnecting member, indicated by arrows 51, can be from about 0.003 to 0.009 inches. The length from the double-curved portion to the shoulder region, indicated by arrow 52, can be from about 0.05 to 0.10 inches. The length from the shoulder region to the top of the peak portion, indicated by arrow 53, can be from about 0.05 to 0.10 inches. The width of the peak portions (unexpanded) indicated by arrows 54, can be from about 0.012 to 0.040 inches. These same dimensions would apply specifically to the embodiments of the present invention shown in FIGS. 6 and 7 and the embodiment of FIGS. 8 and 9.

Referring now to FIG. 12 the width of the strut of the cylindrical element, indicated by arrows 50, can be about from 0.003 to 0.009 inches. The width of the strut of the interconnecting member, indicated by arrows 51, can be from about 0.003 to 0.009 inches. The length from the double-curved portion to the peak portion, indicated by arrow 52, can be from about 0.070 to 0.150 inches. The width of the peak portions indicated by arrow 54, can be from about 0.03 to 0.06 inches.

Due to the thin wall and the small geometry of the stent pattern, it is necessary to have very precise control of the laser, its power level, the focus spot size, and the precise positioning of the laser cutting path. In cutting the strut widths of the embodiment shown in FIGS. 1-5, it is preferable to have a very focused laser spot size which will allow the precise strut pattern to be created on the tubing. For this reason, additional instrumentation which includes a series of lenses may be necessary to be utilized with the laser in order to create the fine focused laser spot necessary to cut that particular pattern.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent. Further details on how the tubing can be cut by a laser are found in U.S. Pat. No. 5,759,192 (Saunders) and U.S. Pat. No. 5,780,807 (Saunders), which have been assigned to Advanced Cardiovascular Systems, Inc. and are incorporated herein by reference in their entirety.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

After the stent has been cut by the laser, electrical chemical polishing, using various techniques known in the art, should be employed in order to create the desired final polished finish for the stent. The electropolishing will also be able to take off protruding edges and rough surfaces which were created during the laser cutting procedure.

Referring now to FIGS. 13-16 there are shown alternative stent pattern designs in accordance with an alternative embodiment of the present invention. For stenting in the carotid arteries it has been discovered that a specialized stent pattern is desired. More specifically it is desirable to have a stent pattern design such that the ends of the stent are very flexible while the center portion of the stent is stiffer. Additionally, but having such a "hybrid" stent design, the scaffolding presented to the wall of the artery can be varied through pattern changes to address specific needs. A hybrid stent design can be performed in many different manners, for example the pattern can be adjusted between "open cell" and "closed cell" patterns, adjusting the cell size between large and small, adjusting the cell geometry and strut diameter. An example of such open cell and closed cell patterns is disclosed in U.S. Pat. No. 5,827,321 (Roubin), the contents of which is hereby incorporated by reference in its entirety. Additionally, a hybrid stent may be constructed of one or more materials.

Figure 13:
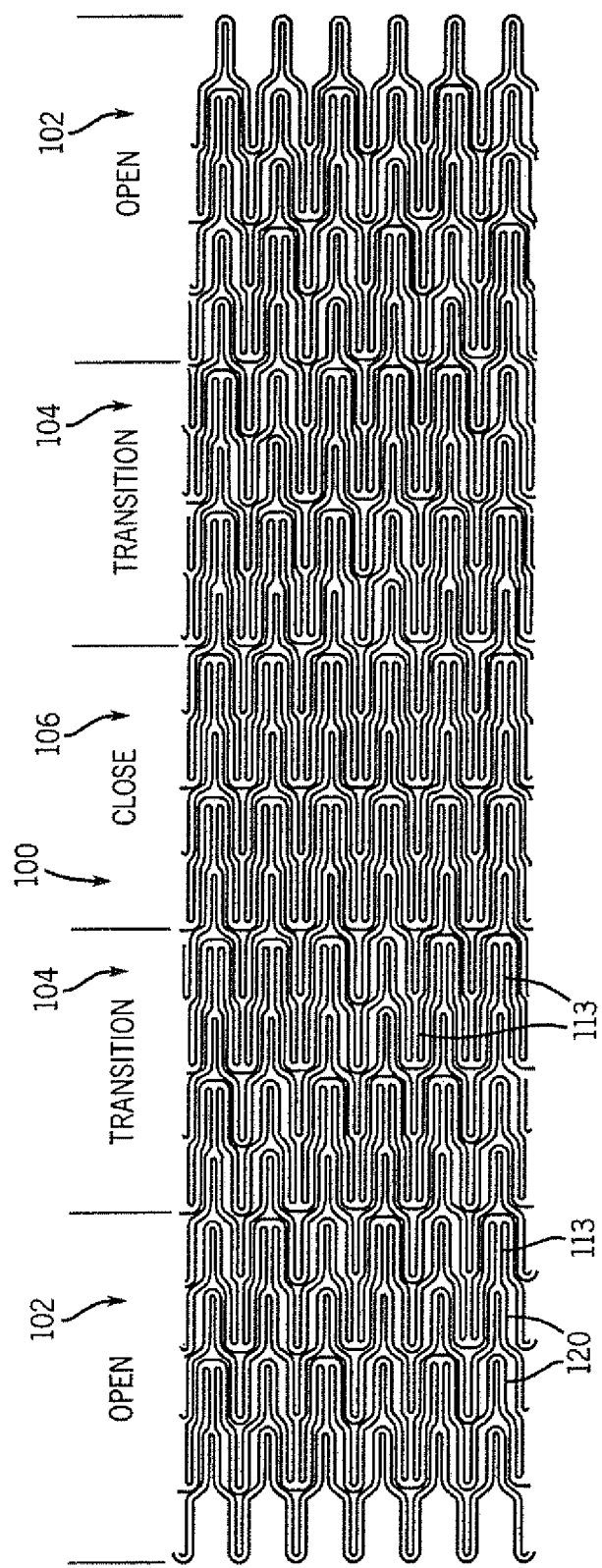
FIG. 13 is a plan view of an alternative hybrid stent design in accordance with the present invention.

Referring now to FIG. 13, there is shown a design for a hybrid stent in accordance with the present invention. As shown in FIG. 13, the hybrid design includes a plurality of transition zones along the length of the stent wherein the pattern changes from an open cell design to a closed cell design then back to an open cell design.

Figure 14:
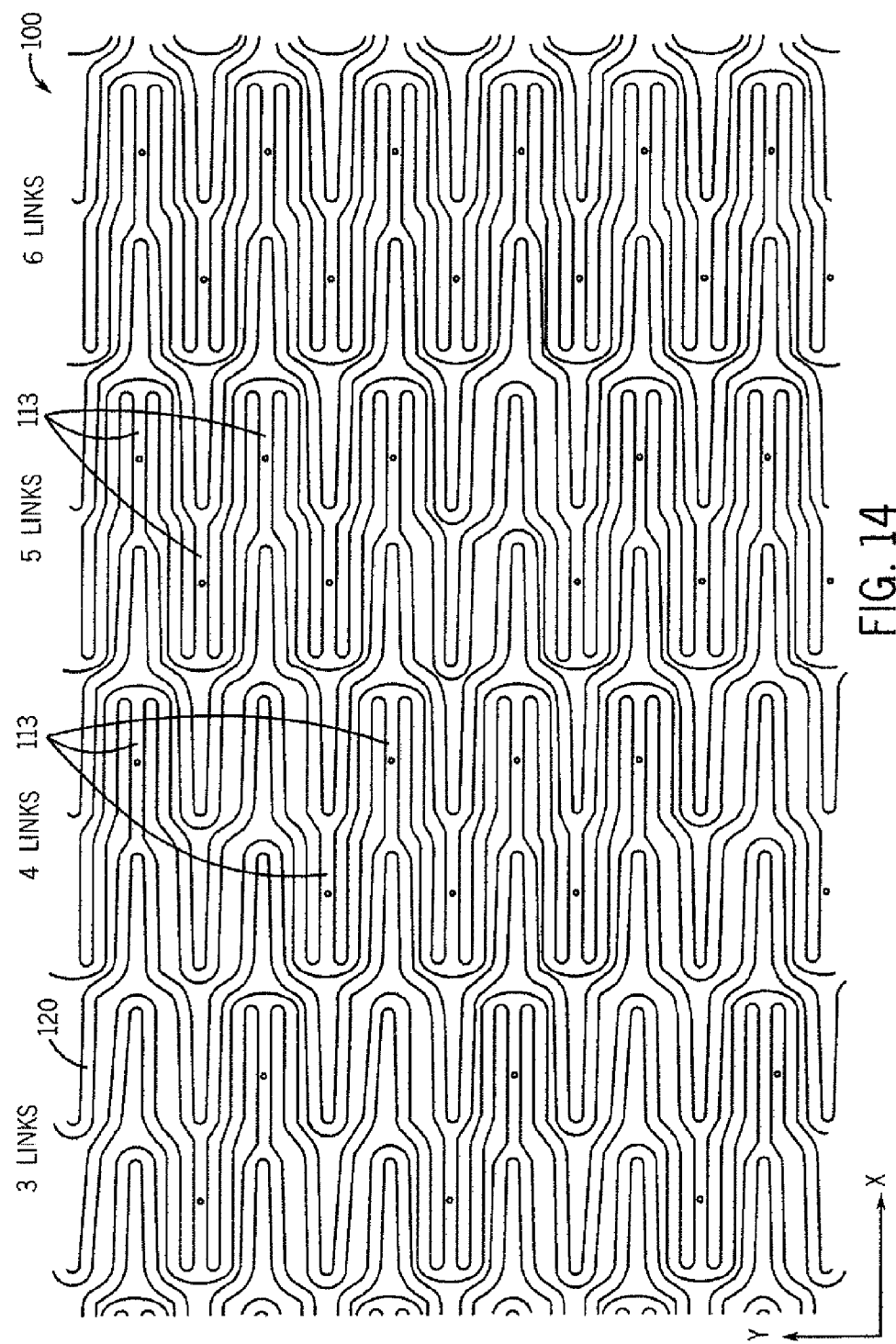
FIG. 14 is a partial plan view of an alternative hybrid stent design in accordance with the present invention.

Referring to FIGS. 13 and 14 there is shown an exemplary embodiment of a hybrid stent in accordance with the present invention, wherein the stent 100 is constructed of a plurality of radially expandable cylindrical elements 120 disposed generally coaxially and interconnected by interconnection members 113. As shown in the figures and particularly in FIG. 14, the number of interconnection members 113 can be varied between each of the adjacent radially expandable cylindrical elements 120 to form the various sections as labeled in FIG. 13. For example, for the open sections (102), the number of interconnection members 113 disposed between the adjacent cylindrical elements 120 is far fewer than the number of interconnection members 113 in transition section 104 and in the closed section 106. The closed section 106 includes an interconnection member extending between each adjacent peak or valley of the adjacent cylindrical members 120. By varying the number of interconnection members 113 as shown in FIGS. 13 and 14 the flexibility of the stent as well as the scaffolding ability of the stent can be varied. If a hybrid stent was produced without the transition section 104, the flexibility of the stent would not be linear along the length of the stent, instead there would be peaks in flexibility curve which would be undesirable.

Figure 15A:
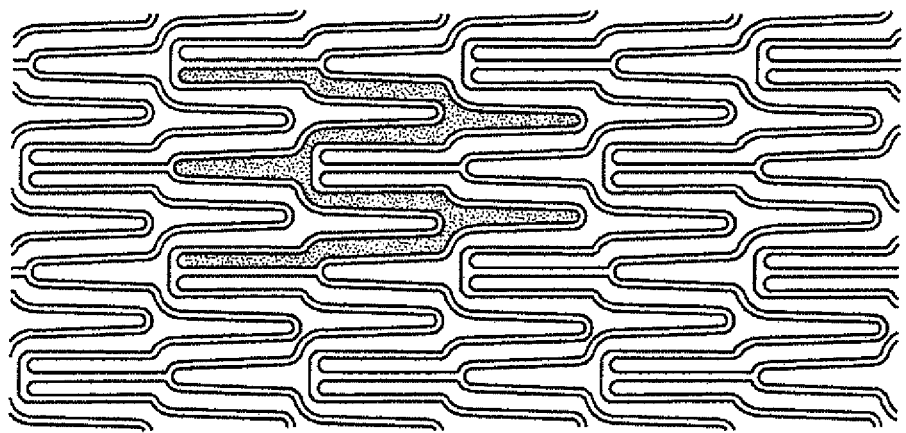
FIGS. 15a and 15b is a plan view of an alternative hybrid stent design in accordance with the present invention illustrating the unit cells.
Figure 15B:
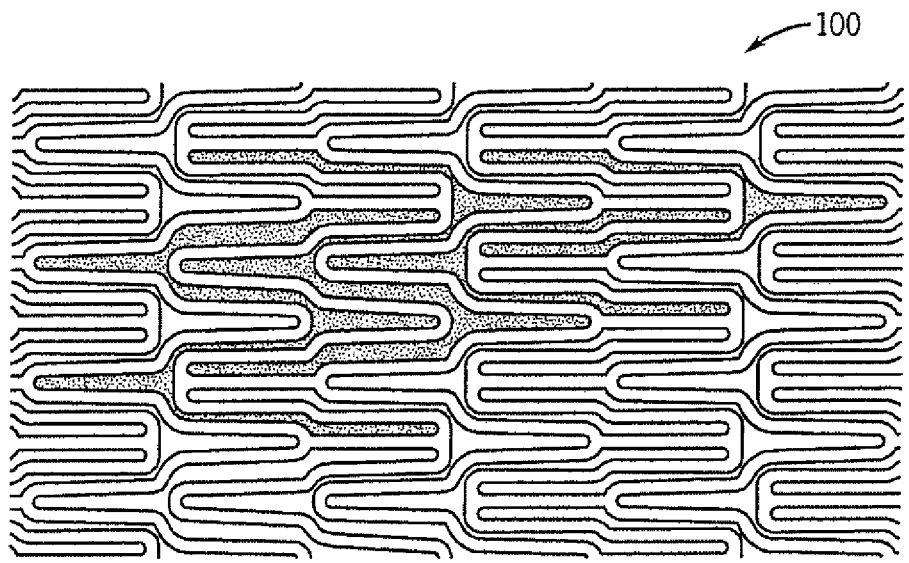

Referring now to FIGS. 15a and 15b, there is shown an exemplary embodiment of a prior art design and the unit cell thereof (darkened portion) and an exemplary embodiment of the hybrid stent design in accordance with the present invention. As shown in FIG. 15a, the stent design shown therein includes a single unit cell which extends along the length of the stent in a repeated pattern. By contrast, the hybrid stent 100 of FIG. 15b illustrates the four different unit cells thereof, illustrating the difference between the open cell and closed cell and transition cell of the exemplary stent pattern.

Figure 16:
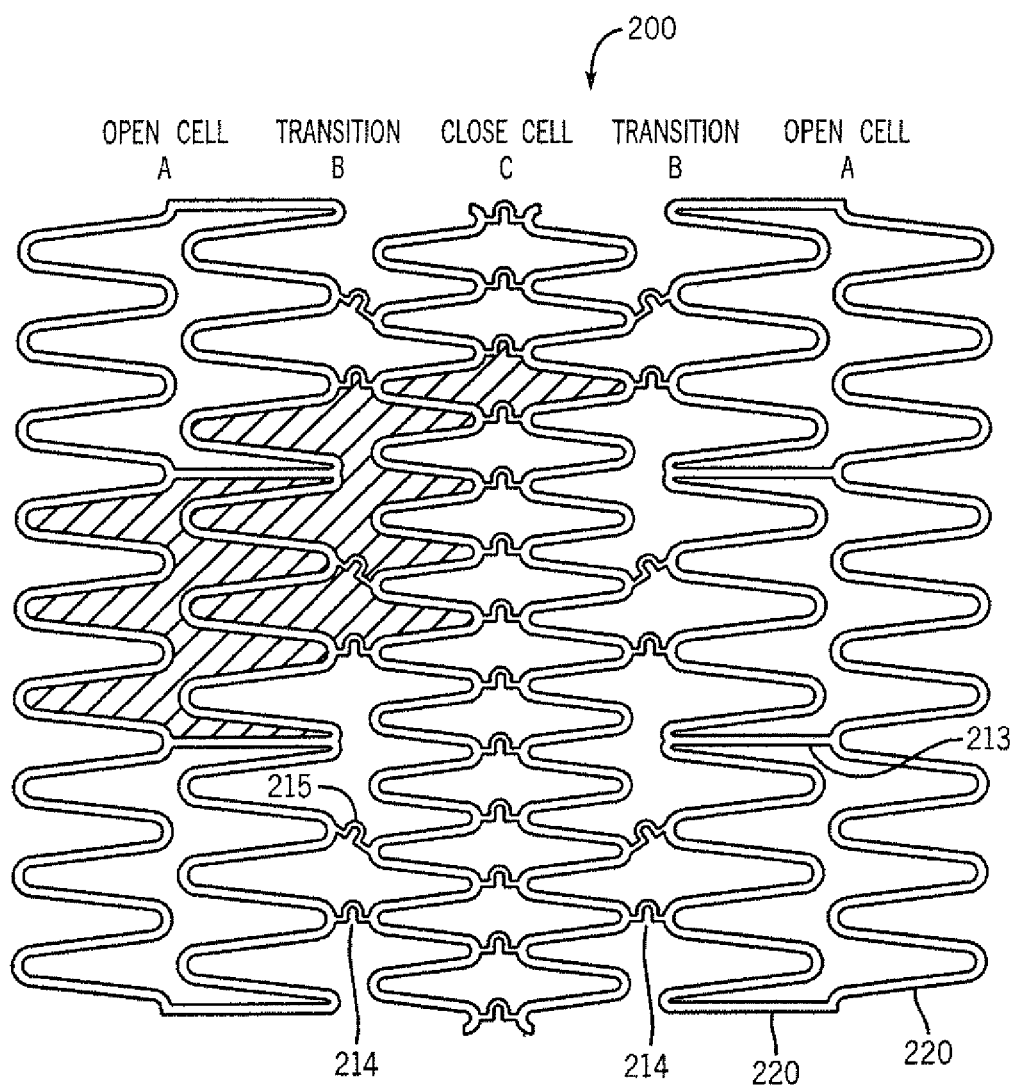
FIG. 16 is a plan view is a plan view of an alternative hybrid stent design in accordance with the present invention.

Referring now to FIG. 16 there is shown yet another exemplary embodiment of a hybrid stent in accordance with the present invention. As shown in FIG. 16, the hybrid stent 200 includes a plurality of cell designs along a length thereof, wherein only a portion of the stent has been shown for simplicity. As shown, the stent includes an open cell portion, a transition section and a closed cell portion. The interconnection members 213 maybe embodied in the form of linear elements extending between adjacent cylindrical members 220 or may include a feature formed therein as shown at 214. Further still, the interconnection members may be disposed at an angle to an axis of the stent as shown by reference number 215. The feature formed in the interconnection members maybe formed to compensate for foreshortening or to aid in flexibility or to transition flexibility along the length of the stent.

Figure 17:
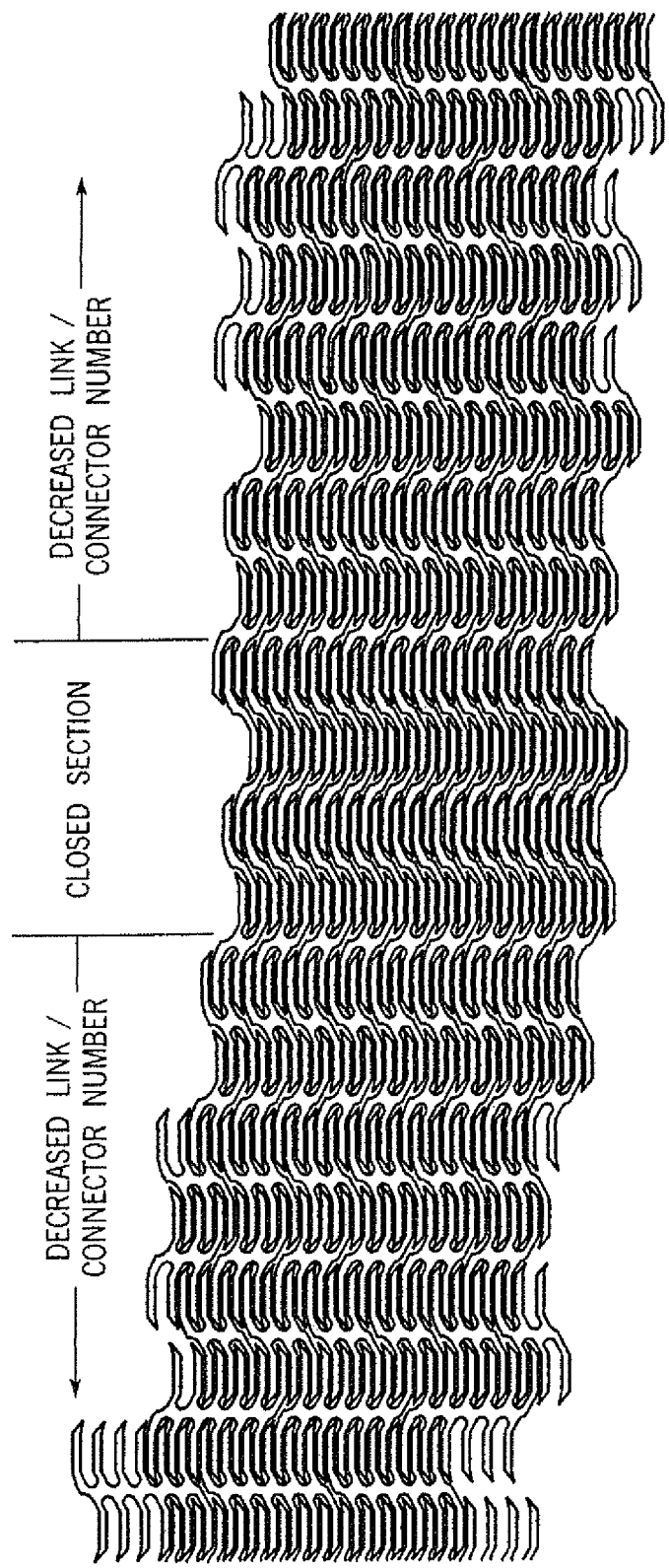
FIG. 17 is a plan view of an alternative hybrid stent design in accordance with the present invention.

Referring now to FIG. 17, there is shown yet another exemplary embodiment of an alternative hybrid stent design in accordance with the present invention. As shown in FIG. 17, the hybrid stent shown therein includes a varying number of interconnection members adjacent to the ends of the stent, whereby the pattern of the stent can be transitioned between an open cell design and a closed cell design.

It shall be understood that the cylindrical members shown in the embodiments herein are merely exemplary and that multiple types of cylindrical members have been shown herein to illustrate the concepts of the present invention.

While the invention has been illustrated and described herein in terms of its use as intra vascular stents, it will be apparent to those skilled in the art that the stents can be used in other instances in all conduits in the body, such as, but not limited to, the urethra and esophagus. Other modifications and improvements may be made without departing from the scope of the invention.

The invention claimed is:

1. A delivery system comprising:
   a delivery catheter having a proximal end and a distal end; and
   a stent disposed at the distal end of the delivery catheter, the stent including:
      a plurality of radially expandable rings disposed adjacent to one another to define a tubular member having a proximal end portion, and a distal end portion, and a middle portion, each of the radially expandable rings including a plurality of strut members;
      at least one interconnection member disposed between a first expandable ring and a second radially expandable ring and extending between strut members thereof at an end portion of the tubular member to define an open cell bordered by the at least one interconnection member and three or more struts of the first expandable ring and of the second radially expandable ring, respectively;
      a plurality of interconnection members included in the middle portion of the tubular member and extending between longitudinally adjacent expandable rings, the number of the plurality of the interconnection members in the middle portion of the tubular member being greater than that of the end portion of the tubular member, and
      wherein a transition section is defined between the end portion and the middle portion, the transition section including at least one open cell defined between at least two longitudinally adjacent expandable rings of the transition section and at least one closed cell defined between the at least two longitudinally adjacent expandable rings, each open cell bordered by circumferentially adjacent interconnection members extending between two longitudinally adjacent expandable rings of the transition section and by three or more struts of each of the two longitudinally adjacent expandable rings, respectively, and each closed cell bordered by circumferentially adjacent interconnection members extending between the two longitudinally adjacent expandable rings and by two struts of each of the two longitudinally adjacent expandable rings.

2. The delivery system of claim 1, wherein the middle portion of tubular member of the stent comprises the plurality of interconnection members disposed between longitudinally adjacent radially expandable rings to define closed cells therebetween, each closed cell bordered by circumferentially adjacent interconnection members and by two struts of each of the longitudinally adjacent rings of the middle portion.

3. The delivery system of claim 1, wherein the at least one closed cell and the at least one open cell of the transition section of the tubular member of the stent are disposed circumferentially adjacent to each other.

4. The delivery system of claim 1, wherein at least one of the plurality of radially expandable rings of the stent includes a W shaped portion at a location adjacent to the at least one interconnection member.

5. The delivery system of claim 1, wherein at least two adjacent expandable rings of the plurality of radially expandable rings include a W shaped portion and a U shaped portion.

6. The delivery system of claim 1, wherein at least one of the distal expandable ring and the proximal expandable ring of the stent includes strut members defining a W shaped portion.

7. The delivery system of claim 1, wherein the at least one of the plurality of radially expandable rings of the stent includes a W shaped portion defined by strut members, an inverted U shaped portion defined by strut members, and a U shaped portion defined by strut members.

8. The delivery system of claim 7, wherein at least one of the plurality of radially expandable rings of the stent includes alternating W shaped portions and U shaped portions along at least a portion of the length of the ring.

9. The delivery system of claim 1, wherein a plurality of interconnection members of the stent are configured to form a continuous spine which extends from the proximal end to the distal end of the stent.

10. The delivery system of claim 1, wherein at least one of the plurality of radially expandable rings of the stent includes at least one shoulder region extending from a valley portion to a peak portion.

11. The delivery system of claim 10, wherein the peak portion is expandable.

12. The delivery system of claim 11, wherein the number of interconnection members between each of the longitudinally adjacent expandable rings differ from each other.

13. The delivery system of claim 1, wherein the at least one interconnection member includes a non-linear portion.

14. The delivery system of claim 1, wherein the stent is self-expandable.

15. The delivery system of claim 14, wherein the stent is made from Nitinol.

16. The delivery system of claim 1, wherein the stent is balloon-expandable.

17. The delivery system of claim 1, wherein the delivery catheter includes an inner tubular member upon which the stent is mounted.

18. The delivery system of claim 1, wherein the delivery catheter includes a retractable sheath.

19. The delivery system of claim 18, wherein the delivery catheter includes an inner tubular member upon which the stent is mounted, and wherein the retractable sheath extends over the stent.

20. The delivery system of claim 1, wherein the delivery catheter includes a balloon upon with the stent is mounted.

* * * * *